(12) United States Patent
Gonda

(10) Patent No.: US 9,592,220 B2
(45) Date of Patent: *Mar. 14, 2017

(54) DIAGNOSIS AND TREATMENT METHODS FOR ENTRY OF GASTROINTESTINAL CONTENTS INTO RESPIRATORY TRACT

(71) Applicant: ARADIGM CORPORATION, Hayward, CA (US)

(72) Inventor: Igor Gonda, San Francisco, CA (US)

(73) Assignee: Aradigm Corporation, Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/204,719

(22) Filed: Mar. 11, 2014

(65) Prior Publication Data

US 2014/0194502 A1 Jul. 10, 2014

Related U.S. Application Data

(63) Continuation-in-part of application No. 13/162,344, filed on Jun. 16, 2011, now Pat. No. 9,372,198.

(60) Provisional application No. 61/777,933, filed on Mar. 12, 2013, provisional application No. 61/777,955, filed on Mar. 12, 2013, provisional application No. 61/355,859, filed on Jun. 17, 2010, provisional application No. 61/370,588, filed on Aug. 4, 2010.

(51) Int. Cl.

| | | |
|---|---|---|
| G01N 33/52 | (2006.01) |
| A61K 31/352 | (2006.01) |
| A61B 5/08 | (2006.01) |
| A61B 5/00 | (2006.01) |
| G01N 33/68 | (2006.01) |
| A61B 5/145 | (2006.01) |
| A61B 5/15 | (2006.01) |

(52) U.S. Cl.
CPC ............ *A61K 31/352* (2013.01); *A61B 5/082* (2013.01); *A61B 5/145* (2013.01); *A61B 5/14507* (2013.01); *A61B 5/4211* (2013.01); *G01N 33/6893* (2013.01); *A61B 5/150015* (2013.01); *G01N 2800/06* (2013.01); *Y10T 436/142222* (2015.01)

(58) Field of Classification Search
CPC ..................................................... G01N 33/52
See application file for complete search history.

(56) References Cited

U.S. PATENT DOCUMENTS

2007/0068810 A1* 3/2007 Tsukashima et al. ......... 204/433
2010/0216754 A1* 8/2010 Hill ............................... 514/171

OTHER PUBLICATIONS

Aswania e al., Relative Bioavailability of Sodium Cromoglycate to the Lung Following Inhalation, Using Urinary Excretion; British Journal of Clinical Pharmacology, vol. 47 (1999) pp. 613-618.
Messerli et al., Cromolyn and Deep Inspiration-Induced Bronchoconstriction; Pneumonology, vol. 153 (1975) pp. 73-80.

* cited by examiner

*Primary Examiner* — Rosanne Kosson
(74) *Attorney, Agent, or Firm* — Convergent Law Group LLP

(57) ABSTRACT

A method of diagnosing in a subject for the purpose of determining if the subject's gastrointestinal contents has entered the subject's respiratory tract. The qualitative analysis can be also expanded into quantitative analysis, enabling the estimation of either the concentration, or the amount, or both, of the gastrointestinal contents that entered the respiratory tract. The invention also provides methods of treatment based on the identification of aspiration using the methods of the invention.

38 Claims, No Drawings

DIAGNOSIS AND TREATMENT METHODS FOR ENTRY OF GASTROINTESTINAL CONTENTS INTO RESPIRATORY TRACT

CROSS-REFERENCE TO RELATED APPLICATIONS

The present application claims priority to U.S. Provisional Ser. No. 61/777,933, filed Mar. 12, 2013, U.S. Provisional Ser. No. 61/777, 955, filed Mar. 12, 2013, and is a Continuation-In-Part of U.S. Ser. No. 13/162,344, filed Jun. 16, 2011 which claims priority to U.S. Provisional Ser. No. 61/355, 859, filed Jun. 17, 2010, and U.S. Provisional Ser. No. 61/370,588, filed Aug. 4, 2010, all of which are incorporated by reference herein.

FIELD OF THE INVENTION

The invention relates generally to the field of medical diagnoses and more particularly to methods and materials used for the detection of entry of gastrointestinal contents into the respiratory tract, with special attention to the diagnosis for the purpose of prevention and treatment of disease.

BACKGROUND OF THE INVENTION

Gastro esophageal reflux disease (GERD) is a condition in which some of the stomach contents (solid and/or liquid) move backwards from the stomach into the esophagus (the tube from the mouth to the stomach). This action can irritate the esophagus, causing heartburn and other symptoms.

Gastroesophageal reflux disease (GERD), gastro-oe-sophageal reflux disease (GORD), gastric reflux disease, or acid reflux disease is defined as chronic symptoms or mucosal damage produced by the abnormal reflux of stomach acid to the esophagus. A typical symptom is heartburn.

This is commonly due to transient or permanent changes in the barrier between the esophagus and the stomach. This can be due to incompetence of the lower esophageal sphincter, transient lower esophageal sphincter relaxation, impaired expulsion of gastric reflux from the esophagus, or a hiatal hernia.

A different type of acid reflux which produces respiratory and laryngeal manifestations is laryngopharyngeal reflux (LPR), also called extraesophageal reflux disease (EERD). Unlike GERD, LPR is unlikely to produce heartburn, and is thus sometimes called silent reflux.

The gastrointestinal contents may thus also enter the respiratory tract as a result of any condition that causes the backward movement of the gastrointestinal contents from the stomach to esophagus. The gastrointestinal contents contain many substances that are likely to be harmful to the respiratory tract: acid, digestive enzymes, microorganisms, allergens, proinflammatory subtances and so on. There is increasing evidence that gastro esophageal reflux disease (GERD) is the underlying mechanism behind many disease conditions of the respiratory tract, such as infections and high morbidity in subjects with lung transplants, asthma, bronchitis, bronchiectasis, pulmonary fibrosis and so on. At present, there are no acceptable methods to detect the entry of gastrointestinal (GI) contents into the respiratory tract.

SUMMARY OF THE INVENTION

Diagnostic formulations for use in diagnosing and treating entry of gastrointestinal contents into the respiratory tract ("aspiration") in subjects, with special attention to the diagnosis for the purpose of prevention and treatment of diseases associated with aspiration. The subjects that may be diagnosed and/or treated using such methods are animals, preferably mammals, including humans.

In a first embodiment, the concentration of the gastrointestinal contents entering the respiratory tract can be estimated by adding a detectable non-toxic label that is not absorbed from the gastrointestinal tract or from the respiratory tract. The label should be in a form that is biocompatible with the respiratory tract and the gastrointestinal tract. The label also should not be destroyed in the gastrointestinal or respiratory tract. If the contents of the gastrointestinal tract enters the respiratory tract, the respiratory fluid can be sampled (e.g., by bronchoscopy) and the concentration of the label in the respiratory tract can be measured, thus estimating the concentration of the gastrointestinal contents that entered the respiratory tract.

For example, the diagnostic formulation may be comprised of an ingestible liquid; and a plurality of particles comprised of a biocompatible polymer such as carnauba wax and a non-radioactive label such as fluorescein.

Accordingly, a first embodiment provides a method of diagnosing respiratory fluid in a subject, comprising orally administering to a subject a diagnostic formulation comprising a plurality of particles, wherein the particles comprise a biocompatible material that is not destroyed in the gastrointestinal or respiratory tracts and a detectable label, allowing the formulation to remain in the subject over a period of time during which the subject would be expected to aspirate the formulation from the gastrointestinal tract into the respiratory tract, accessing respiratory fluid from the subject, and analyzing the respiratory fluid to determine if the fluid contains the detectable label. The formulation optionally comprises an aqueous carrier.

In certain aspects, the biocompatible material comprises carnauba wax. In other aspects, the biocompatible material is associated with a detectable label, e.g. a fluorescent label, a radioactive label, a magnetic label and a UV label. In a specific aspect, the detectable label is an optically fluorescent label, e.g. fluorescein. The label is preferably encapsulated in a material which is not degraded in the respiratory and gastrointestinal tracts. In a specific aspect, the label is encapsulated in carnauba wax.

The the respiratory fluid n the methods of the invention used is accessed in any manner that allows analysis of fluid from the respiratory tract of the subject. In preferred aspects, the body fluid analyzed is fluid collected, e.g., using bronchoscopy, spontaneous sputum collection or induced sputum production. In some aspects, the analyzing of the detectable label in the collected respiratory fluid comprises determining a number of labels per unit volume of respiratory fluid obtained from the subject.

In certain embodiments, the methods of the invention further comprise the administration of a control formulation to a subject to establish a level of the agent for analysis of the presence and/or concentration of gastric contents in the respiratory fluid of a subject either before or following administration of the diagnostic formulation. The control formulation may be administered by inhalation, e.g., to establish levels of an agent that may be present should the agent be aspirated. The control formulation also may be administered by ingestion to establish a baseline for the agent should it not be aspirated. For the latter aspect, the control formulation is preferably administered during a period of time when the subject is not expected to experience aspiration of gastrointestinal contents into the respiratory tract.

In a specific aspect, detection of the level of the agent or detectable label indicative of aspiration of gastrointestinal contents into the respiratory tract requiring medical intervention is based on a comparison of the level observed following administration of the diagnostic formulation and the level observed following administration of the control formulation. In the case of administration of the control formulation to establish a negative baseline, the level of agent or detectable label determined for administering to the subject a medical treatment to reduce or prevent such aspiration is determined as an increased level of agent over that seen following the control administration. In the case of the control administration establishing the level in a bodily fluid, the level of agent or detectable label determined for administering to the subject a medical treatment to reduce or prevent such aspiration is determined by comparison to the levels produced using the control formulation.

In another aspect, detection of the level of the agent or detectable label indicative of aspiration of gastrointestinal contents into the respiratory tract requiring medical intervention is based on ranges established through clinical practice. This can be based on the levels of aspiration detected in a range of previous patients or a range based on a simlulation of predicted values of agent and/or detectable label.

In specific aspects, the invention provides a method of diagnosing respiratory fluid in a subject suffering from gastroesophageal reflux disease (GERD), comprising orally administering to a subject suspected of suffering from gastro esophageal reflux disease (GERD) a formulation comprised of a plurality of particles comprised of fluorescein and carnauba wax. allowing the formulation to remain in the subject over a period of time during which the subject would be expected to aspirate the formulation from the gastrointestinal tract into the respiratory tract, accessing respiratory fluid from the subject, and analyzing the respiratory fluid to determine the presence of fluorescein, thereb determining if the subject aspirates gastrointestinal contents into the respiratory tract.

The invention further comprises a method of determining the respiratory fluid contains a concentration of gastric contents indicative of aspiration of gastrointestinal contents into the respiratory tract and administering to the subject a medical treatment to reduce or prevent such aspirations. Such medical treatments can include pharmacological intervention or surgical intervention.

In specific embodiments, the invention provides a diagnostic formulation, comprising an ingestible liquid carrier; and a plurality of particles comprised of carnauba wax and a detectable label. The formulation prefereably comprises an aqueous carrier. The detectable labe can be, e.g., a fluorescent label, a radioactive label, a magnetic label and a UV label. In a specific aspect, the particles comprise fluorescein encapsulated in carnauba wax. A preferred label is flourescein. In another specific aspect, the particles comprise a radioactive material encapsulated in carnauba wax. In a preferred aspect, the label is encapsulated in a material which is not degraded in the respiratory and gastrointestinal tracts.

In other embodiments, the invention provides a method of treating a subject suffering from entry of gastrointestinal contents orally administering to a subject a formulation comprising a plurality of particles, wherein the particles comprise a biocompatible material that is not destroyed in the gastrointestinal or respiratory tracts and a detectable label, allowing the formulation to remain in the subject over a period of time during which the subject would be expected to aspirate the formulation from the gastrointestinal tract into the respiratory tract; accessing respiratory fluid from the subject, and analyzing the respiratory fluid to determine the concentration of detectable label in the respiratory fluid; determining if the concentration of detectable label in the respiratory fluid is indicative of aspiration of gastrointestinal contents into the respiratory tract requiring pharmacological treatment, and administering to the subject a pharmacological treatment to reduce or prevent such aspirations.

In preferred aspects, the the respiratory fluid is accessed by collecting fluid from lungs of the subject. In certain aspects, the analyzing comprises determining a number of fluorescein particles per unit volume of respiratory fluid obtained from the subject.

In certain embodiments, the invention provides for dual use of an agent that is not absorbed from the gastrointestinal tract of a subject but is absorbed from the respiratory tract for estimating the amount of the gastrointestinal contents that entered the respiratory tract, and particles of a biocompatible material that is not destroyed in the gastrointestinal or respiratory tracts and a detectable label to estimate the concentration of gastrointestinal contents that entered the respiratory tract. In certain aspects, these agents and particles can be used in the same formulation. The administered agent could then be detected using a bodily fluid (e.g., blood, a blood product or urine) and the particles detected in, e.g., the sputum or bronchial fluid of a subject. Using both approaches of the method of the invention will allow the determination of both the amount of gastric contents that has aspirated into a subject's respiratory system, and the concentration of the gastric contents in the bodily fluid.

For example, a formulation containing both particles of label-encapsulated carnauba wax and an agent such as a cromolyn salt may be administered to a subject. Following administration, the analysis of the cromolyn salt in the subject, e.g., through analysis of blood or urine, can be used to determine the amount of gastric contents aspirated into the respiratory system while the analysis of the detectable label in the bodily fluid of the subject, e.g. through detection of the label in sputum, can determine the concentration of the gastric contents in the bodily fluid.

The present invention also provides a method of determining the amount and concentration of gastric contents in the respiratory fluid of a subject, comprising orally administering to a subject a formulation comprising a plurality of particles, wherein the particles comprise a biocompatible material that is not destroyed in the gastrointestinal or respiratory tracts and a detectable label, and an agent that is not absorbed from the gastrointestinal tract of a subject but is absorbed from the respiratory tract of the subject, allowing the formulation to remain in the subject over a period of time during which the subject would be expected to aspirate the formulation from the gastrointestinal tract into the respiratory tract, accessing the respiratory fluid from the subject, analyzing the respiratory fluid to determine the concentration of the detectable label in the respiratory fluid, accessing a body fluid other than respiratory fluid from the subject, and analyzing the body fluid to determine if the fluid contains a level of the agent indicative of the amount of aspiration of gastrointestinal contents into the respiratory tract. The body fluid other than respiratory fluid can be urine, blood or blood products.

The invention also futher provides determining the respiratory fluid contains a concentration of gastric contents in the respiratory tract indicative of aspiration of gastrointestinal contents into the respiratory tract, and administering to the subject a medical treatment to reduce or prevent such aspirations. Such medical treatments can include pharmacological intervention or surgical intervention.

Alternatively, the diagnostic methods of the invention may employ an agent that is not absorbed from the gastrointestinal tract, but is absorbed from the respiratory tract. Levels of this agent in a subject's bodily fluid, e.g., blood, plasma, serum or urine, can be detected and used to estimate the amount of the gastrointestinal contents that entered the respiratory tract. This is done by measuring the amount of the agent that has entered the circulation (from the respiratory tract) by taking samples of blood, plasma, serum or urine, and quantifying the amount of the label in those fluids. If the drug is excreted also into saliva, then the saliva samples may be the most convenient method. For example, cromolyn sodium (sodium cromoglycate) is a harmless substance that is soluble in water, is not destroyed in the gastrointestinal tract or the respiratory tract, is not absorbed from the gastrointestinal tract but is absorbed from the respiratory tract. A water solution of cromolyn sodium can therefore be swallowed and the concentrations of cromolyn in blood and urine samples can be used to estimate the amount of gastrointestinal contents that entered the respiratory tract. Cromolynic acid and other salts of cromolyn can be used instead of sodium cromolyn, or substances that are structurally similar such as nedocromil sodium. Another class of substances that have members that are poorly absorbed from the gastrointestinal tract but are well absorbed from the lung are anticholinergic drugs also known as muscarinic acid receptor antagonists such as tiotropium bromide.

Accordingly, the invention provides a method of diagnosing respiratory fluid in a subject, comprising orally administering to a subject a diagnostic formulation comprising an agent that is not absorbed from the gastrointestinal tract of a mammal but is absorbed from the respiratory tract of a mammal, allowing the formulation to remain in the subject over a period of time during which the subject would be expected to aspirate the formulation from the gastrointestinal tract into the respiratory tract, accessing a body fluid from the subject, and analyzing the body fluid to determine if the fluid contains a level of the agent indicative of aspiration of gastrointestinal contents into the respiratory tract.

In a more specific aspect, the invention provides a method of diagnosing respiratory fluid in a subject, comprising orally administering to a subject a diagnostic formulation comprising a cromolyn salt, allowing the diagnostic formulation to remain in the subject over a period of time during which the subject would be expected to aspirate the formulation from the gastrointestinal tract into the respiratory tract, accessing a body fluid from the subject; and analyzing the body fluid to determine if the fluid contains a level of the cromolyn salt indicative of aspiration of gastrointestinal contents into the respiratory tract.

The invention also provides methods of treating subjects in need of medical intervention due to aspiration of gastic contents into repiratory fluid. Accordingly, the invention provides a method of treating a subject suffering from entry of gastrointestinal contents into the respiratory tract, comprising orally administering to a subject a diagnostic formulation comprising an agent that is not absorbed from the gastrointestinal tract of a mammal but is absorbed from the respiratory tract of a mammal, allowing the formulation to remain in the subject over a period of time during which the subject would be expected to aspirate the formulation from the gastrointestinal tract into the respiratory tract, accessing a body fluid from the subject wherein the body fluid, analyzing the body fluid to determine the level of the agent in the body fluid, determining the fluid contains a level of the agent salt indicative of aspiration of gastrointestinal contents into the respiratory tract, and administering to the subject a pharmacological or surgical treatment to reduce or prevent such aspirations, or advising the subject to change their diet, timing of meals, body posture at night and so on to minimize or prevent the aspiration of gastrointestinal fluid into the respiratory tract. One or both of the diagnostic agengs, such as fluorescein encapsulated in carnauba wax particles or cromolyn solution, either individually, or as a mixture, can be subsequently administered to probe the effectiveness of the intervention to treat the condition of aspiration of gastro-intestinal fluid into the respiratory tract.

The invention also provides a method of treatment, comprising detecting a level of cromolyn salt indicative of aspiration of gastrointestinal contents into the respiratory tract, and administering to the subject a pharmacological or surgical treatment, or other interventions to reduce or prevent such aspiration. The invention also provides a method treating a subject suffering from entry of gastrointestinal contents into the respiratory tract, comprising orally administering to a subject a diagnostic formulation comprising a cromolyn salt allowing the formulation to remain in the subject over a period of time during which the subject would be expected to aspirate the formulation from the gastrointestinal tract into the respiratory tract, accessing a body fluid from the subject, and analyzing the body fluid to determine the level of cromolyn salt in the body fluid, determining the fluid contains a level of cromolyn salt indicative of aspiration of gastrointestinal contents into the respiratory tract, and administering to the subject a pharmacological or surgical treatment to or other intervention to reduce or prevent such aspirations.

The invention also provides administering a control formulation comprising the agent used in the diagnostic formulation to the subject at an occasion different to that when the orally administered diagnostic formulation is administered, accessing a body fluid from the subject following the administration of the control formulation, and analyzing the body fluid to determine if the fluid contains the agent.

The control formulation can be administered orally or by inhalation. Preferably, the body fluid analyzed is collected following the administration of the control formulation and prior to analyzing the body fluid. In some aspects, the control formulation is administered during a period of time when the subject is not expected to experience aspiration of gastrointestinal contents into the respiratory tract. In other aspects, the control formulation is administered during a period of time when the subject is expected to experience aspiration of gastrointestinal contents into the respiratory tract. In yet other aspects, the control formulation is a positive control administered to determine the amount of agent expected to be detected in a bodily fluid should aspiration occur.

A particular aspect of the invention involves the use of dipstick technology in order to assay for the presence of an agent such as cromolyn in a body fluid such as urine or saliva. When the dipstick indicates the presence of the agent such as cromolyn the presence of such is a positive result indicating that the subject is aspirating contents of the gastrointestinal tract into the respiratory tract of the subject. Those skilled in the art will appreciate that a wide range of different embodiments of dipstick technologies can be used in connection with the invention. Examples of such dipstick assays are disclosed within U.S. Pat. No. 5,256,372 issued Oct. 26, 1993; U.S. Pat. No. 4,968,604 issued Nov. 9, 1990;

and U.S. Pat. No. 7,972,837 issued Jul. 5, 2011, all of which are incorporated herein by reference as are the patents and publications cited within these patents.

The dipstick assay methodology generally requires the presence of a paper or cardboard substrate which is dipped into a solution to be tested. The substrate allows for the solution to migrate upward by capillary action. Although different embodiments are possible, the substrate generally includes a reagent that will interact with cromolyn so that an observable effect is generated to detect cromolyn at least qualitatively, and preferably quantitatively. One example is that the dipstick substrate contains a reagent that reacts with the agent such as cromolyn, where the reaction gives rise to a distinct color which can be readily detected by an unaided human eye under normal room lighting. The intensity of this color is the measure of the amount of the agent in solution. Some intermediate steps may also be required to cause and enhance the formation of the color reaction. Such chemistry was described for example by K Görlitzer, G Badia, P G Jones. Pharmazie. 2001 May; 56 (5):401-6.

Another method uses an antibody which binds to a particular agent such as cromolyn with respect to the present invention. The substrate may include an anti-antibody which binds to the antibody that binds the agents such as cromolyn. Further, the antibody or anti-antibody generally includes a visually detectable label wherein the label can be readily detected by an unaided human eye under normal room lighting. The system may show a negative response when a signal or line across the paper appears at a particular location and a positive response when a signal such as a line appears at a different location on a substrate paper.

Certain devices can be used in the methods of the invention. Multiple forms of dipstick devices may be used to carry out the present invention.

In a first aspect, the dipstick device for the detection of an agent indicative of aspiration of gastrointestinal contents into the respiratory tract of a subject, comprising a substrate comprised of paper a first antibody which binds to an agent that is not absorbed from the gastrointestinal tract of a subject but is absorbed from the respiratory tract of a subject, a second antibody which binds to the first antibody; and a visually detectable label.

In another aspect, the dipstick device for the detection of an agent indicative of aspiration of gastrointestinal contents into the respiratory tract of a subject comprises a substrate comprised of paper and a first reagent that reacts with the agent to form a second reagent optically distinguishable from the first reagent. In a specific aspect, the first agent is a colored dye and the second reagent is a color distinguishable from the color of the first agent.

In another aspect, the dipstick device for the detection of an agent indicative of aspiration of gastrointestinal contents into the respiratory tract of a subject comprises a substrate comprised of paper and a first reagent that reacts with the agent, and a second reagent that enables the reaction of the first reagent to form a dye with the agent that is of a different color than the color either the first or the second reagent.

In another aspect, the dipstick device for the detection of an agent indicative of aspiration of gastrointestinal contents into the respiratory tract of a subject comprises a substrate comprised of paper and a reagent that reacts with the agent to form a compound with a visually detectable color.

In another aspect, the dipstick device for the detection of an agent indicative of aspiration of gastrointestinal contents into the respiratory tract of a subject comprises a substrate comprised of paper and a first reagent that reacts with the agent and a second reagent that enables the reaction of the first reagent to form a compound with a visually detectable color.

The dipstick devices of the invention generally detect a specific agent, e.g., cromolyn salts, cromolynic acid, nedocromil, nedocromil salts and muscarinic acid receptor antagonists.

Those skilled in the art will know that other methods of detection can be used based on various properties of the specific agents. Portable electronic technology devices including cellphones, smartphones, tablets and so on can be used to detect unique optical properties of the diagnostic agents in the collected body fluids. The subject being diagnosed can read the result on the electronic device, or the signal can be transmitted to a specialized center for analysis, or to a healthcare professional.

Both the agent and the particle approaches can be also used purely for qualitative purposes to detect the entry of gastrointestinal contents into the respiratory tract. A label that is destroyed neither in the respiratory tract, nor in the gastrointestinal tract and which also has the properties of being absorbed from the respiratory tract but not from the gastrointestinal tract, can be used for qualitative detection of the entry of gastrointestinal contents into the respiratory tract. Such a label is swallowed and its presence is detected in the blood samples, or in urine if it is excreted via kidneys from blood to urine. Alternatively, a label that is not absorbed or destroyed in the gastrointestinal and respiratory tracts can be swallowed and subsequently detected in the respiratory fluid if the subject suffers from a condition that moves the contents of the gastrointestinal tract into the respiratory tract.

Although GERD is generally referred to here, those skilled in the art will understand that this invention is applicable to use in connection with any disorder that causes entry of gastrointestinal contents into the respiratory tract of the subject. Different subjects may be suffering from different disorders which result in involuntary aspiration of gastrointestinal contents. This may result in some of the gastrointestinal contents entering the respiratory tract of the subject causing damage. The present invention is intended to detect the presence of such gastrointestinal contents in the respiratory tract regardless of a particular disease or disorder which may have resulted in the presence of the gastrointestinal contents in the respiratory tract. The invention also describes medical interventions, e.g., surgical or pharmacological interventions, to prevent the entry of gastrointestinal tract contents into the respiratory tract.

A method of diagnosing respiratory fluid in a subject suffering from gastro esophageal reflux disease (GERD) is disclosed. The method comprises (1) orally administering to a subject suspected of suffering from aspiration of gastrointestinal fluid into the respiratory tract, e.g., subjects at high risk who have gastro esophageal reflux disease (GERD), or subjects with respiratory condition of unknown origin, a formulation comprised of a plurality of particles comprised of a biocompatible material (e.g. carnauba wax) and a detectable label (e.g. a fluorescent label), (2) allowing the formulation to remain in the subject over a period of time during which the subject would be expected to regurgitate formulation, (3) collecting respiratory fluid from the subject, and (4) analyzing the respiratory fluid to determine if the fluid contains the detectable label, and thereby determining if the subject aspirated gastrointestinal contents into the respiratory tract.

Those skilled in the art will know that there are numerous ways in which the label contained within the material of the particles that are digested neither in the gastrointestinal tract, nor in the respiratory tract, can be detected. External counters can detect the presence of radiolabel in such particles in the respiratory fluid. Alternatively, magnetic detectors can be used for magnetic labels, or the magnetic particles can be extracted with a magnet and their quantity determined, e.g., by weighing or counting them. The preferred embodiment is to use fluorescein in the label contained in carnauba wax particles. The respiratory fluid can be heated to melt the carnauba wax and the fluorescein released from the particles can then be detected using its fluorescent properties. Other extraction methods that incorporate the use of organic solvents to dissolve or extract the carnauba wax can be employed.

By carrying out the steps as described above it is possible to analyze the fluid collected from the respiratory tract and determine the concentration of the label in the respiratory fluid. The higher the concentration of the label in the respiratory fluid the greater the potential damage to the subject's respiratory tract due to involuntary aspiration of gastrointestinal contents. Higher concentrations of the label may suggest more aggressive treatment of the subject.

In another embodiment of the invention, the formulation is also orally administered to the subject. However, instead of comprising particles with a fluorescent label (or other label) coated with carnauba wax (or other material) the formulation comprises a substance (an agent) such as cromolyn sodium. Cromolyn sodium is water soluble and harmless. Further, cromolyn sodium is not absorbed in the gastrointestinal tract, but is absorbed from the respiratory tract into the blood stream. Those skilled in the art will recognize other compounds which have these characteristics. However, it is important to select compounds that are known not to affect in that particular subject, or in that group of subjects, the aspiration of gastrointestinal contentss into the respiratory tract. When the formulation of such an agent that is not causing or preventing aspirations is orally administered to the subject and there is aspiration of gastrointestinal contents into the respiratory tract, it is possible to test for the presence of the agent in the subject's blood or urine.

Thus, in accordance with this embodiment of the method the respiratory fluids of the subject does not need to be extracted. This method allows for theestimation of the total amount of gastrointestinal contents which has entered the respiratory tract.

An example of a substance that is safe to both the respiratory tract and the gastrointestinal tract is cromolyn sodium. Cromolyn is in fact a drug with very few adverse reactions. Cromolyn sodium is thought to act by inhibiting of the release of histamine and leukotrienes (SRS-A) from the mast cell. It is therefore possible that in some subjects the cause of aspiration of the gastrointestinal tract contents into the respiratory tract is inhibited by the action of cromolyn sodium and similar drugs. This desirable pharmacological effect can be detected for example by administering orally to the subject on one occasion carnauba wax particles coated with fluorescein alone and on another occasion these particles together with cromolyn sodium. If on the first occasion the carnauba wax particles are detected in the respiratory tract fluids such as the sputum from the subject but they are not detected when such particles are co-administered with cromolyn, then this suggests that cromolyn is minimizing or blocking the aspiration of gastrointestinal contents into the respiratory tract. Of course, those skilled in the art will know that other types of biocompatible, non-reactive substances can be used instead of carnauba wax, fluorescein or cromolyn sodium.

When a substance such as a cromolyn sodium is administered to the subject it may be advisable to first administer a control formulation of cromolyn sodium orally to the subject in the morning. The dose is orally administered at a time when the subject would not be expected to experience any reflux. After administering the formulation such as cromolyn sodium the subject is not allowed to sleep or even lie down. Further, any steps that may need to be taken in order to avoid the subject experiencing reflux into the respiratory tract are taken. Blood and urine samples are then taken during the day and analyzed as a control. It may be that no cromolyn appears in the blood or urine. However, if a small amount appears, then that level of cromolyn can be used as a baseline to compare to the level when the formulation is administered and the subject is allowed to lie down, sleep and normally experience reflux into the respiratory tract. When the second administration occurs the same amount of cromolyn sodium is orally administered as was administered in the control. Carrying out a comparison will avoid false positives in the diagnosis of the subject, particularly in subjects that have abnormally high oral absorption of cromolyn. It is also possible to maximize the probability of aspiration in a particular subject, for example with heavy meals or foods that provoke GERD. It is pointed out that in most "normal" subjects there will be substantially no absorption of cromolyn into the blood or urine unless the cromolyn is absorbed via the respiratory tract.

Yet another means to establish whether the subject is likely to be suffering from the aspiration of gastrointestinal contents into the respiratory tract is to establish the amounts and concentration of the diagnostic substances in trials in which a group of subjects with aspirations documented by other methods such as video monitoring via bronchoscopy or gamma scintigraphic detection in the respiratory tract of ingested radioactive substances, are compared with the quantities detected in healthy subjects who do not have such aspiration. Threshold levels of these diagnostic markers above which the aspiration is likely can thus be established.

In yet another embodiment of the invention the two embodiments described above (coated particles and cromolyn sodium) are combined. Thus, the composition which is orally administered to the subject is a liquid formulation which includes the labeled particles coated with the biocompatible material such as carnauba wax and a material such as cromolyn sodium dissolved in the surrounding aqueous carrier. In accordance with this method follow-up analysis involves testing the respiratory fluid for the presence of the labeled particles to determine the concentration of the label in the fluid, and testing the blood and/or urine of the subject in order to calculate the total amount of gastrointestinal contents which was aspirated into the respiratory tract.

The combination method described above can, of course, also be carried out using the control. The control is carried out as described above or the cromolyn sodium formulation is administered to the subject purely as a control and samples of the subject's blood and/or urine are taken during a period of time when the subject is not expected to experience reflux, such as during the day when the subject is not lying down or sleeping.

In still another embodiment of the invention the labeled material is coated with a composition which does not degrade inside the human body but which can be removed or degraded readily outside the human body by the application of heat or other chemicals. More specifically, the material coating the label does not melt at body temperature may be removed by the application of heat at a temperature above body temperature (>40° C.) or by the application of compound which readily dissolves the composition coating the label.

In yet another aspect of the invention positive controls can be used. For example, the subject can be administered a cromolyn formulation by inhalation. By knowing the amount of cromolyn administered into the subject's respiratory tract, and thereafter testing for cromolyn in the subject's blood and urine a comparison can be made to later tests when the cromolyn will be absorbed from reflux out of the subject's stomach into the respiratory tract. It is also, of course, possible to carry out both a negative and a positive control on the same subject.

The invention includes a method of diagnosing respiratory tract fluid in a subject by first orally administering to a subject a formulation comprised of a plurality of particles comprised of a biocompatible material and a detectable label. The formulation may include any number of particles, but for example 100, 500, 1,000 or more, 10,000 or more, 100,000 or more particles. The biocompatible material may be carnauba wax or a different non-reactive biocompatible polymer and the formulation may be an aqueous carrier which may be simply water. The label is preferably a non-toxic label such as a fluorescent label that is encapsulated within the biocompatible material. The label may also be a radioactive label, a magnetic label and/or a UV labeled material. After administering the formulation the subject is allowed to rest during a period of time where aspiration of the formulation from the gastrointestinal tract into the respiratory tract would be expected to occur. After this time respiratory fluid is extracted from the subject such as by the use of bronchoscophy. Alternatively, the subject may spontaneously produce sputum as a sample of respiratory fluid and the labeled particles are then detected in this body fluid. Yet another option is to induce sputum production by one of the methods known to be used for this purpose, such as inhalation of hypertonic saline. The respiratory fluid collected from the subject is then analyzed in order to determine if the fluid contains the detectable label present within the formulation which was orally administered. The presence of the formulation label indicates that the subject has experienced aspiration of the gastrointestinal contents into the respiratory tract.

If the diagnosis is thus made, then it may be advisable to start treating the subject to minimize or eliminate the aspiration of gastro-intestinal contents into the respiratory tract, or at least to minimize the adverse effects of such aspirations.

There are several types of interventions to prevent or reduce aspirations or minimize them and their effects that have been described. Medical treatments for use with the present invention include pharmacologic treatments and surgical treatments. The three main types of medicines to treat GERD are antacids, H2RAs (histamine type 2 receptor antagonists), and PPIs (proton pump inhibitors). Exemplary pharmacologic treatments that can be used with the invention include administration of H2Ras, e.g., Famotidine, Nizatidine, Ranitidine, or Cimetidine; or proton pump inhibitors, e.g., Omeprazole, Lansoprazole, Pantoprazole, Rabeprazole, Esomeprazole, or Dexlansoprazole. Surgical treatments include fundoduplication and endoscopic techniques. Other forms of intervention include assistance with the institution of lifestyle changes in the subject, including changes to a subject's sleeping circumstances or other behavior modification (e.g., dietary changes, changes in consumption of drugs or alcohol, and the like).

It is common for patients suspected of having recurrent GERD with aspiration simply to be treated with a proton-pump inhibitor to reduce the acidity of gastric contents. While this is effective for reflux esophagitis, it is ineffective for the consequences of aspiration of the other components of gastric contents, including food particles and digestive enzymes. Effective prevention of microaspiration secondary to GERD would require surgical intervention, such as gastric fundoplication. At present, the impact of surgical interventions in GERD with microaspiration is difficult to assess without a simple, direct diagnostic test. The present invention therefore combines diagnosis of aspirations with a medical intervention such as gastric fundoplication or pharmacological treatment. A milder intervention may be change in the timing, quality and quantity and food and drinks for the subject, sleeping position and so on. The impact of these interventions can be monitored using the methods described in this invention, with diagnostic substances such as a fluorescent marker encapsulated in small particles made from a non-digestable biocompatible matrix, or solutions of substances such as cromolyn sodium which is chemically stable in the body, safe and well tolerated, poorly absorbed from the gastrointestinal tract but well absorbed from the respiratory tract.

An aspect of the invention is that it is safe, and convenient for the subject.

Another aspect of the invention is that it is easily administered even in a primary healthcare setting, fast and cost-effective, with high specificity and selectivity. The use of simple "dipstick" methods is particularly attractive: the subject is given a dose of the substance such as cromolyn, then urine is collected from the subject. A dipstick is placed in contact with the urine sample, followed by minimum manipulation and observation of changes in the dipstick appearance indicative of the presence and quantity of the diagnostic substance, such as cromolyn sodium.

Another aspect of the invention is that it avoids the use of radiolabels, because they are not practicable in a routine setting and multiple exposures to radioactivity raises safety concerns.

Another aspect of the invention is that to be able to estimate the concentration of the gastrointestinal contents that entered the respiratory tract, it is necessary to to avoid the use of labels that enter the blood circulation.

Another aspect of the invention is that it uses labels that stay as a tracer of the GI fluids that enter into the respiratory tract and remain intact in the GI and respiratory tracts.

Another aspect of the invention is that it uses materials presented in forms that are safe in the respiratory and GI tracts.

Another aspect of the invention is that it retains the label while in the body, presents the label readily when outside the body to a detector providing high specificity and selectivity (i.e., only the label material that was initially swallowed or otherwise placed into the GI tract and then enter the respiratory tract will be detected).

Another aspect of the invention is that the label used can be detected even if only minute quantities of the gastrointestinal materials entered the respiratory tract.

Another aspect of the invention is that the diagnostic method to detect the presence of aspirations of gastrointestinal contents into the respiratory tract is used in a subject and if the result is positive, treatment of the condition starts. The impact of the treatment can be then also evaluated with the diagnostic method.

Yet another aspect of the invention is to use two different diagnostic methods to eliminate the possibility that a substance used in the diagnostic test itself is having an effect on aspirations of gastro-intestinal contents into the respiratory tract.

Another aspect of the invention is that if one of the substances used as a diagnostic test is found to be reducing or eliminating the aspirations, then that substance can be used as the agent to minimize or prevent aspirations.

These and other objects, advantages, and features of the invention will become apparent to those persons skilled in the art upon reading the details of the methods and formulations as more fully described below.

DETAILED DESCRIPTION OF THE INVENTION

Before the present methods and formulations are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a particle" includes a plurality of such particles and reference to "the label" includes reference to one or more labels and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention includes different methods for diagnosing respiratory fluid in a subject wherein the respiratory fluid has been regurgitated from the gastrointestinal tract from the subject. The method includes orally administering to a subject a formulation comprised of a plurality of particles which particles are comprised of a biocompatible material such as a biocompatible polymer or a wax such as a caruba wax wherein the particles include some type of detectable lable which may be a fluorescent label, a radioactive label, a magnetic label or a UV detectable label. The formulation is allowed to remain in the subject over a period of time during which the subject would be expected to aspirate the formulation from the gastrointestinal tract. For example, the subject might be administered the formulation just prior to going to sleep. After allowing for sufficient time respiratory fluid is extracted from the patient. That respiratory fluid is analyzed in order to determine if it contains the detectable label.

Once the patient has been determined as aspirating fluid from the gastrointestinal tract into the respiratory tract the patient will require treatment. That treatment involves orally administering to the subject a formulation which comprises a pharmacological substance. That pharmacological substance or pharmaceutically active drug is administered in order to reduce or prevent aspiration of fluid from the gastrointestinal tract into the respiratory tract. The pharmaceutically active drug is preferably a drug which acts locally on the gastrointestinal tract and is not absorbed systemically. Examples of such drugs are drugs selected from the group consisting of cromolyn salts, cromolynic acid, nedocromil, nedocromil salts or muscarinic acid receptor antagonist.

Dosing of the drug to the patient will vary depending on a wide range of factors including the patient's age, size, weight, sex and condition. However, dosing of the drug to the patient is generally carried out by oral administration of the drug in the form of pills, capsules or solutions. Pills and capsules may contain the drug in combination with a pharmaceutically acceptable excipient. Solutions or suspensions may contain the drug in an aqueous solution or suspension with pharmaceutically acceptable carriers.

The oral formulation may be administered to the subject just prior to going to bed at night. Further, additional doses may be administered during the night depending on the subjects responsiveness to the medication. The dose may be administered before and/or after an activity such as going to sleep which is likely to result in aspirations. That activity can be going to sleep for the evening, taking an afternoon nap, or after eating a large meal or drinking heavily.

In one embodiment of the invention patients undergoing lung transplants are treated prophylactically in order to reduce or prevent intestinal fluid into the newly transplanted lung.

The dosing amount will also vary with the particular drug. When administering cromolyn and in particular cromolyn salts currently marketed safe dosages for children for other indications have been shown to be in the range of about 20 mg 4 times per day to 40 mg 4 times per day. Adults have been dosed in the amount of 200 mg 4 times per day to 400 mg 4 times per day.

The formulation may include both an immediate release component where a drug is immediately released and a controlled release component where the drug is not released immediately (e.g. over the first hour) but released gradually during hours 2 to about 8 hours after administration. Oral liquid formulations can be viscous formulations which provide a degree of coating to the gastrointestinal tract.

When administering cromolyn in order to carry out diagnostics the cromolyn should be delivered with significant amount of water, e,g. 6 oz or more, 12 oz or more, 16 oz or more of water. However, when the cromolyn is being administered in order to treat the subject it is preferably delivered in the absence of water or with a very small amount of water e.g. 4 oz or less, 2 oz or less, 1 oz or less.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Fluorescein-Spray Drying

Prepare nuclei of <1 micron fluorescein particles by spray drying aqueous solutions of fluorescein. Then condense vapors of respiratory-tract compatible waxes such as carnauba was upon the fluorescein particles completely encapsulating the fluorescein. Make a suspension of these particles in water using usual pharmaceutical methods to stabilize these, add flavor etc. Subject swallows a precise amount of the liquid suspension prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. The fluorescent label is then released either as a result of the addition of a suitable solvent, or by increasing the temperature to dissolve the wax, or both.

The concentration of material in the respiratory tract entering due to reflux is estimated from the intensity of fluorescence using one of many detectors for fluorescence. The important parameter is the concentration of the fluorescent label per volume of the airway fluid in which it was contained as that is likely to be related to the harmful effects of the gastrointestinal contents in the respiratory tract.

Example 2

Fluorescein-Flow Focusing

Prepare nuclei of <1 micron fluorescein particles by extruding a biocompatible wax (carnauba) in an outer tube and a fluorescein label in an inner tube in order to completely encapsulate the fluorescein. Details of the flow focusing method are described in U.S. Pat. No. 6,116,516 and related issued patents, all of which are incorporated herein by reference. Make a suspension of these particles in water using usual pharmaceutical methods to stabilize these, add flavor etc. Subject swallows a precise amount of the liquid suspension prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. The fluorescent label is then released either as a result of the addition of a suitable solvent, or by increasing the temperature to dissolve the wax, or both.

The concentration of material in the respiratory tract entering due to reflux is estimated from the intensity of fluorescence using one of many detectors for fluorescence. The important parameter is the concentration of the fluorescent label per volume of the airway fluid in which it was contained as that is likely to be related to the harmful effects of the gastrointestinal contents in the respiratory tract.

Example 3

Magnetic Particles-Flow Focusing

Magnetic particles may be suspended in a formulation and then swallowed for the diagnostic purposes described in this invention. However, it may be desirable to protect these particles from digestion in the gastrointestinal tract. Further, unencapsulated magnetic particles could be harmful to either the gastrointestinal tract, or the respiratory tract, or both. Using the flow focusing method it is possible to manufacture biocompatible encapsulated magnetic particles that are not digested in the gastrointestinal tract. Prepare nuclei of <1 micron magnetic particles by extruding a biocompatible wax (carnauba) in an outer tube and a magnetic particle label in an inner tube in order to completely encapsulate the magnetic particle. Make a suspension of these particles in water using usual pharmaceutical methods to stabilize these, add flavor etc. Subject swallows a precise amount of the liquid suspension prior to activity that is causing GIT reflux (e.g., prior to going to sleep).

The health care provider takes a sample of airway fluid through induced coughing, bronchoscopy, spontaneous coughing etc. The concentration of the gastrointestinal contents in the respiratory tract can be estimated by collecting with a magnet the magnetic particles and then counting them using one of the many methods available for such counting, or by measurement of the total magnetism. The sample may be also diluted in additional water, or a solvent that dissolves the wax. The magnetic particles can then be released either as a result of the addition of a suitable solvent, or by increasing the temperature to dissolve the wax, or both.

The important parameter is the concentration of the magnetic particle label per volume of the airway fluid in which it was contained as that is likely to be related to the harmful effects of the gastrointestinal contents aspirated into the respiratory tract.

Example 4

UV Labeled Particles-Flow Focusing

Prepare nuclei of <1 micron UV labeled particles by extruding a biocompatible wax (carnauba) in an outer tube and a UV label or UV labeled particle in an inner tube in order to completely encapsulate the UV labeled particle. Make a suspension of these particles in water using usual pharmaceutical methods to stabilize these, add flavor etc. Subject swallows a precise amount of the liquid suspension prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. The UV labeled particle is then released either as a result of the addition of a suitable solvent, or by increasing the temperature to dissolve the wax, or both.

The amount of material in the respiratory tract entering due to reflux is estimated from the UV labeled particles detected using standard detectors. The important parameter is the concentration of the UV labeled particles per volume of the respiratory fluid in which it was contained as that is likely to be related to the harmful effects of the gastrointestinal contents aspirated into the respiratory tract.

Example 5

Phosphorescent Particles-Flow Focusing

Prepare nuclei of <1 micron phosphorescent labeled particles by extruding a biocompatible wax (carnauba) in an outer tube and a phosphorescent labeled particle in an inner tube in order to completely encapsulate the phosphorescent labeled particle. Make a suspension of these particles in water using usual pharmaceutical methods to stabilize these, add flavor etc. Subject swallows a precise amount of the liquid suspension prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. The phosphorescent labeled particle is then released either as a result of the addition of a suitable solvent, or by increasing the temperature to dissolve the wax, or both.

The amount of material in the respiratory tract entering due to reflux is estimated from the phosphorescent labeled particles detected using standard detectors. The important parameter is the concentration of the phosphorescent labeled particles per volume of the airway fluid in which it was contained as that is likely to be related to the harmful effects of the gastrointestinal contents aspirated into the respiratory tract.

Example 6

Fluorescein-Flow Focusing with Cromolyn Sodium)

Prepare nuclei of <1 micron fluorescein particles by extruding a biocompatible wax (carnauba) in an outer tube and a fluorescein label in an inner tube in order to completely encapsulate the fluorescein. Make a suspension of these particles in water using usual pharmaceutical methods to stabilize these, dissolve cromolyn sodium and add flavor etc. Subject swallows a precise amount of the liquid suspension including the dissolved cromolyn sodium prior to activity that is causing GIT reflux (e.g., prior to going to sleep).

The health care provider takes a sample of airway fluid through induced coughing, bronchoscopy, spontaneous coughing etc. The sample may be diluted in additional water, or a solvent that dissolves the wax. Fluorescein is then released either as a result of the addition of a suitable solvent, or by increasing the temperature to dissolve the wax, or both.

If the carnauba wax particles were suspended in a solution of cromolyn, blood or urine samples are also taken and checked for cromolyn to estimate the total amount of gastrointestinal contents that entered the respiratory tract. The amount of cromolyn in the blood or urine shows how much of the formulation of cromolyn swallowed did enter the respiratory tract, because cromolyn will not enter the blood stream, or urine,via the GI tract.

The fluorescein particles encapsulated in carnauba wax enter the respiratory tract if the subject aspires the contents of her/his gastrointestinal tract. Fluorescein can be released from the carnauba wax particles present in the respiratory fluid by heating or dissolving the wax using organic solvents. The concentration of material in the respiratory tract entering due to such aspiration is estimated using one of many methods to detect and quantify fluorescein. The important parameter is the concentration of fluorescein per volume of the airway fluid in which it was contained as that is likely to be related to the harmful effects of the gastrointestinal contents aspirated into the respiratory tract. The presence of cromolyn in a body fluid such as plasma, serum or preferably urine can be quantified by a variety of methods used to measure cromolyn concentrations, such as HPLC with a suitable detector or radioimmunoassay. Measurement of samples of body fluid enables to estimate the total amount of cromolyn that entered the respiratory tract, and therefore provides an estimate of the total amount of gastrointestinal fluid that entered the patient's respiratory tract. Therefore, the combination of the two diagnostic agents provides estimates of both the concentration of the gastrointestinal fluid in the respiratory tract as well as the total amount of the contents of gastrointestinal fluid that entered the respiratory tract.

Example 7

Treatment of Aspirations of Gastrointestinal Contents into the Respiratory Tract The subject swallows prior to going to bed an aqueous suspension of carnauba wax particles that contain encapsulated fluorescein. The subject then collects any sputum that has been spontaneously produced overnight. If insufficient sputum is obtained, the subject is administered a mist of hypertonic saline by inhalation to induce sputum production. The sputum sample is diluted with a high pH buffer and organic solvent immiscible with water is added to extract the wax. The aqueous phase is separated and a sample is analyzed for fluorescence using a fluorescence detector such as a fluorimeter. If the fluorescence intensity exceeds the limit previously established for healthy subjects, it is assumed that the subject who has just undergone the test suffers from aspirations of gastrointestinal contents into the respiratory tract. The test may need to be repeated several times in case the aspirations do not occur every night, especially if the subject already has a condition that is suspected to cause such aspirations, or the subject has respiratory symptoms of aspirations. When the diagnosis is confirmed, the subject takes (prior to going to bed) a dose of cromolyn sodium and collects urine samples overnight as well as the first thing in the morning. The subject then either sends the urine sample for analysis of cromolyn to a laboratory, or uses a dipstick test at home. The subject repeats the test for several days. If the amount of cromolyn detected in the urine does not exceed the amounts typically found in subjects without aspirations, or the cromolyn concentration in the urine continues to get smaller upon successive testing, it may be concluded that cromolyn (in this subject) is effective to minimize or prevent aspirations of gastric contents into the respiratory tract and it will be therefore used for this purpose for as long as the condition exists, or the treatment ceases to be effective.

Example 8

Treatment of Aspirations of Gastrointestinal Contents into the Respiratory Tract The subject swallows prior to going to bed an aqueous suspension of carnauba wax particles that contain encapsulated fluorescein. The subject then collects any sputum that has been spontaneously produced overnight. If insufficient sputum is obtained, the subject is administered a mist of hypertonic saline by inhalation to induce sputum production. The sputum sample is diluted with a high pH buffer and organic solvent immiscible with water is added to extract the wax. The aqueous phase is separated and a sample is analyzed for fluorescence using a fluorescence detector such as a fluorimeter. If the fluorescence intensity exceeds the limit previously established for healthy subjects, it is assumed that the subject who has just undergone the test suffers from aspirations of gastrointestinal contents into the respiratory tract. When the diagnosis is confirmed, the subject takes (prior to going to bed) carnauba wax particles that contain encapsulated fluorescein, suspended in an aqueous solution of cromolyn sodium. The subject then collects a sputum sample in the morning, or goes to a healthcare professional who will collect a sample of the respiratory fluid which is then analyzed for the presence of the fluorescein. If the test is negative, the subject may need to repeat for several days to confirm that the cromolyn prevents or reduces the aspiration of gastrointestinal fluid into the respiratory tract.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treating a mammal suffering from abnormal entry of gastrointestinal contents into the respiratory tract, comprising:
   (a) orally administering to the mammal a diagnostic formulation comprising a diagnostic agent that is not absorbed from the gastrointestinal tract of the mammal but is absorbed from the respiratory tract of the mammal;
   (b) allowing the diagnostic formulation to remain in the mammal over a period of time during which the mammal would be expected to aspirate the formulation from the gastrointestinal tract into the respiratory tract;
   (c) obtaining a sample of a body fluid from the mammal, wherein the body fluid is blood, plasma, serum or urine;
   (d) analyzing the body fluid to detect the level of the diagnostic agent in the body fluid;
   (e) determining that the fluid contains a level of the diagnostic agent indicative of aspiration of gastrointestinal contents into the respiratory tract, and
   (f) providing a pharmaceutical composition to reduce such aspirations in the subject.

2. The method of claim 1, wherein the body fluid is collected prior to analyzing the body fluid.

3. The method of claim 1, wherein the administered diagnostic agent is selected from the group consisting of cromolyn salts, cromolynic acid, nedocromil, nedocromil salts and muscarinic acid receptor antagonists.

4. The method of claim 1, wherein the administered agent is a cromolyn salt.

5. The method of claim 1, further comprising:
   (g) administering a control formulation comprising the same diagnostic agent as found in the diagnostic formulation to the subject at an occasion different to that when the orally administered diagnostic formulation is administered;
   (h) obtaining the body fluid of claim 1 from the subject following the administration of the control formulation, wherein the body fluid is blood, serum, plasma or urine;
   (i) analyzing the body fluid to determine if the body fluid contains the diagnostic agent; and
   (j) determining that the level of diagnostic agent detected following administration of the diagnostic formulation is indicative of aspiration of gastrointestinal contents into the respiratory tract by comparison of the level of the diagnostic agent detected in the body fluid following administration of the diagnostic formulation to the level of diagnostic agent detected in the body fluid following administration of the control formulation.

6. The method of claim 5, wherein the control formulation is administered orally.

7. The method of claim 5, wherein the control formulation is administered by inhalation.

8. The method of claim 5, wherein the body fluid is collected following the administration of the control formulation and prior to analyzing the body fluid.

9. The method of claim 5, wherein the control formulation is administered during a period of time when the subject is not expected to experience aspiration of gastrointestinal contents into the respiratory tract.

10. The method of claim 5, further comprising detecting a level of the diagnostic agent indicative of aspiration of gastrointestinal contents into the respiratory tract based on the level of the diagnostic agent observed following administration of the control formulation.

11. A method of treating a mammal suffering from entry of gastrointestinal contents into the respiratory tract, comprising:
   (a) orally administering to the mammal a diagnostic formulation comprising a cromolyn salt;
   (b) allowing the diagnostic formulation to remain in the mammal over a period of time during which the subject would be expected to aspirate the formulation from the gastrointestinal tract into the respiratory tract;
   (c) obtaining a body fluid from the subject, wherein the body fluid is blood, plasma, serum or urine;
   (d) analyzing the body fluid to detect the level of cromolyn salt in the body fluid;

(e) determining that the fluid contains a level of cromolyn salt indicative of aspiration of gastrointestinal contents into the respiratory tract, and
(f) providing a pharmaceutical composition to reduce such aspirations in the subject.

12. The method of claim 11, wherein the body fluid is collected prior to analyzing the body fluid.

13. The method of claim 11, further comprising:
(g) administering a control formulation comprising the cromolyn salt found in the diagnostic formulation to the subject at an occasion different to that when the orally administered diagnostic formulation is administered;
(h) obtaining the body fluid of claim 11 from the subject following the administration of the control formulation; analyzing the body fluid to determine if the fluid contains the cromolyn salt; and
(i) determining that the level of cromolyn salt detected following administration of the diagnostic formulation is indicative of aspiration of gastrointestinal contents into the respiratory tract by comparison of the level of the cromolyn salt detected in the body fluid following administration of the diagnostic formulation to the level of cromolyn salt detected in the body fluid following administration of the control formulation.

14. The method of claim 13, wherein the control formulation is administered orally.

15. The method of claim 13, wherein the control formulation is administered by inhalation.

16. The method of claim 13, wherein the body fluid is collected following the administration of the control formulation and prior to analyzing the body fluid.

17. The method of claim 13, wherein the control formulation is administered during a period of time when the subject is not expected to experience aspiration of gastrointestinal contents into the respiratory tract.

18. The method of claim 13, further comprising detecting a level of the cromolyn salt indicative of aspiration of gastrointestinal contents into the respiratory tract based on the level of the cromolyn salt observed following administration of the control formulation.

19. A method of treating a mammal suffering from entry of gastrointestinal contents into the respiratory tract, comprising:
(a) orally administering to the mammal a diagnostic formulation comprising a diagnostic agent that is not absorbed from the gastrointestinal tract of the mammal but is absorbed from the respiratory tract of the mammal;
(b) allowing the diagnostic formulation to remain in the mammal over a period of time during which the mammal would be expected to aspirate the formulation from the gastrointestinal tract into the respiratory tract;
(c) obtaining a sample of a body fluid from the mammal, wherein the body fluid is blood, plasma, serum or urine;
(d) analyzing the body fluid to detect the level of the diagnostic agent in the body fluid;
(e) determining that the fluid contains a level of the diagnostic agent indicative of aspiration of gastrointestinal contents into the respiratory tract, and
(f) providing a surgical treatment to reduce such aspirations in the subject.

20. The method of claim 19, wherein the surgical treatment is fundoplication.

21. The method of claim 19, wherein the body fluid is collected prior to analyzing the body fluid.

22. The method of claim 19, wherein the administered diagnostic agent is selected from the group consisting of cromolyn salts, cromolynic acid, nedocromil, nedocromil salts and muscarinic acid receptor antagonists.

23. The method of claim 19, wherein the administered agent is a cromolyn salt.

24. The method of claim 19, further comprising:
(g) administering a control formulation comprising the same diagnostic agent as found in the diagnostic formulation to the subject at an occasion different to that when the orally administered diagnostic formulation is administered;
(h) obtaining a body fluid from the subject following the administration of the control formulation, wherein the body fluid is blood, serum, plasma or urine;
(i) analyzing the body fluid to determine if the body fluid contains the diagnostic agent; and
(j) determining that the level of diagnostic agent detected following administration of the diagnostic formulation is indicative of aspiration of gastrointestinal contents into the respiratory tract by comparison of the level of the diagnostic agent detected in the body fluid following administration of the diagnostic formulation to the level of diagnostic agent detected in the body fluid following administration of the control formulation.

25. The method of claim 24, wherein the control formulation is administered orally.

26. The method of claim 24, wherein the control formulation is administered by inhalation.

27. The method of claim 24, wherein the body fluid is collected following the administration of the control formulation and prior to analyzing the body fluid.

28. The method of claim 24, wherein the control formulation is administered during a period of time when the subject is not expected to experience aspiration of gastrointestinal contents into the respiratory tract.

29. The method of claim 24, further comprising detecting a level of the diagnostic agent indicative of aspiration of gastrointestinal contents into the respiratory tract based on the level of the diagnostic agent observed following administration of the control formulation.

30. A method of treating a mammal suffering from entry of gastrointestinal contents into the respiratory tract, comprising:
(a) orally administering to the mammal a diagnostic formulation comprising a cromolyn salt;
(b) allowing the diagnostic formulation to remain in the mammal over a period of time during which the subject would be expected to aspirate the formulation from the gastrointestinal tract into the respiratory tract;
(c) obtaining a body fluid from the subject, wherein the body fluid is blood, plasma, serum or urine;
(d) analyzing the body fluid to detect the level of cromolyn salt in the body fluid;
(e) determining that the fluid contains a level of cromolyn salt indicative of aspiration of gastrointestinal contents into the respiratory tract, and
(f) providing a surgical treatment to reduce such aspirations in the subject.

31. The method of claim 30, wherein the surgical treatment is fundoplication.

32. The method of claim 30, wherein the body fluid is collected prior to analyzing the body fluid.

33. The method of claim 30, further comprising:
(g) administering a control formulation comprising the cromolyn salt found in the diagnostic formulation to the subject at an occasion different to that when the orally administered diagnostic formulation is administered;

(h) obtaining the body fluid of claim 30 from the subject following the administration of the control formulation;
(i) analyzing the body fluid to determine if the fluid contains the cromolyn salt; and
(j) determining that the level of cromolyn salt detected following administration of the diagnostic formulation is indicative of aspiration of gastrointestinal contents into the respiratory tract by comparison of the level of the cromolyn salt detected in the body fluid following administration of the diagnostic formulation to the level of cromolyn salt detected in the body fluid following administration of the control formulation.

34. The method of claim 33, wherein the control formulation is administered orally.

35. The method of claim 33, wherein the control formulation is administered by inhalation.

36. The method of claim 33, wherein the body fluid is collected following the administration of the control formulation and prior to analyzing the body fluid.

37. The method of claim 33, wherein the control formulation is administered during a period of time when the subject is not expected to experience aspiration of gastrointestinal contents into the respiratory tract.

38. The method of claim 33, further comprising detecting a level of the cromolyn salt indicative of aspiration of gastrointestinal contents into the respiratory tract based on the level of the cromolyn salt observed following administration of the control formulation.

\* \* \* \* \*